US006537795B1

(12) United States Patent
Ståhl

(10) Patent No.: US 6,537,795 B1
(45) Date of Patent: *Mar. 25, 2003

(54) METHOD AND MEANS FOR THE PRODUCTION OF HYALURONIC ACID

(75) Inventor: Sten Ståhl, Lund (SE)

(73) Assignee: Pharmacia AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/496,149

(22) Filed: Feb. 1, 2000

Related U.S. Application Data

(63) Continuation of application No. 08/737,408, filed as application No. PCT/SE95/00585 on May 24, 1995, now Pat. No. 6,090,596.

(30) Foreign Application Priority Data

May 26, 1994 (SE) ................................. 9401806

(51) Int. Cl.$^7$ ................ C12N 15/01; C12N 1/20; C12P 19/04; C12P 19/26
(52) U.S. Cl. ............... 435/253.4; 435/41; 435/84; 435/101; 435/252.1; 435/441; 435/444; 514/54
(58) Field of Search ............ 435/253.4, 252.5, 435/441, 444, 41, 84, 101, 170, 885; 536/55.1

(56) References Cited

U.S. PATENT DOCUMENTS

| 4,141,973 A | 2/1979 | Balazs |
| 4,517,295 A | 5/1985 | Bracke et al. |
| 4,782,046 A | 11/1988 | Brown et al. |
| 5,015,577 A | 5/1991 | Weigel et al. |
| 5,411,874 A | 5/1995 | Ellwood et al. |
| 5,681,825 A | 10/1997 | Lindqvist et al. |
| 6,090,596 A | * 7/2000 | Stahl .................. 435/101 |

FOREIGN PATENT DOCUMENTS

| CA | 1328841 | 4/1994 |
| WO | WO9533067 | 12/1995 |

OTHER PUBLICATIONS

J.B. Woolcock, *The Capsule of Streptococus equi*, Journal of General Microbiology, 85, pp 372–375, 1974, Great Britain.
Pharmacia, *Healon Sodium Hyaluronate*, Product Information.
Wirt, H. et al., *New Aspects in the Surgical Treatment of Glaucomo Comparison of Viscoelastic Substances in Chamber Angle Surgery*, BIOSIS No.: 94126491.

* cited by examiner

*Primary Examiner*—Christopher L. Chin
*Assistant Examiner*—James L. Grun
(74) *Attorney, Agent, or Firm*—Dinsmore & Shohl LLP

(57) ABSTRACT

A method for selecting streptococcus strains capable of producing hyaluronic acid with molecular weight exceeding six million includes the steps of cultivating strains of streptococci individually in culture medium which is free of metal ions which promote degradation of hyaluronic acid and which does not release from the reactor metal ions which promote the degradation of hyaluronic acid; and selecting a supercapsulated strain of a streptococcus, supercapsulated members thereof having a mucoid morphology and being capable of forming capsules having a diameter of greater than 4 μm.

19 Claims, No Drawings

METHOD AND MEANS FOR THE PRODUCTION OF HYALURONIC ACID

This application is a continuation application of Ser. No. 08/737,408, filed Jan. 7, 1997, now U.S. Pat. No. 6,090,596, which is a 35 U.S.C. 371 filing of PCT/SE95/00585, filed May 24, 1995.

TECHNICAL FIELD

The present invention is related to a method for the production of high molecular weight hyaluronic acid by fermentation using supercapsulated strains of streptococci. The invention also relates to a method for the selection of supercapsulated mutants and to mutants producing such hyaluronic acid in high yield.

BACKGROUND ART

Hyaluronic acid (HA) or hyaluronan is a glycosaminoglucan consisting of repeating disaccharides of alternating D-glucuronic acid and N-acetylglucosamine molecules. These molecules are joined by a β(1,3)-D linkage while the glucosamine to glucuronic acid linkage is β(1,4)-D.

There are several sources of hyaluronic acid and its molecular weight varies considerably depending on the source. The HA found in synovial fluid has a molecular weight of about 1 to 8 million, that in human umbilical cord has a molecular weight around 3.6–4.5 million and HA in rooster combs may reach very high values, for instance up to 12–14 million, or even higher. The chemical composition of hyaluronic acid is the same regardless of its source and since it is non-immunogenic it has found several applications in medicine (Brimacombe and Webber (1964)). The effectiveness of HA is a result of an unique combination of elastic and viscous properties, which are correlated to the molecular weight. Therefore, there was early an interest in obtaining as high molecular weights as possible.

Accordingly, the literature contains numerous examples of very high values of the molecular weight of HA but these values very often refer to the source material. It should be noticed, however, that since the HA as produced in biological systems like rooster combs, is associated with proteins and other glycosaminoglycans, for example chondroitin sulphate, it has to be extensively purified. Even if very sophisticaed methods for purification and sterilization, have been developed it is inevitable that the molecular weight decreases during these steps and the final product in most cases has much lower molecular weight.

The major HA product on the market today is Healon® (Pharmacia AB, Uppsala, Sweden) which has a molecular weight around 3.5 million. This product is prepared from rooster combs according to a method based on the disclosure of U.S. Pat. No. 4141973. From the same source is prepared a HA product with a molecular weight around 5 million, Healon® GV (Pharmacia AB). These moleular weights refer to the sterilized products and this means that the product before the sterilization step must have molecular weights around 5 and 7 million, respectively.

There are very few high molecular weight HA products on the market, in spite of the well-documented usefulness of HA in several medical indications, for instance in ophthalmology. One reason for this is probably the complex purification procedures required in order to obtain a pure product from the sources mentioned above, especially rooster combs, without too much degradation of the molecular chains. Therefore, there is a need for alternative sources or production systems which are well controlled and which allow a simplified purification procedure.

Numerous articles and patent applications have been published which relate to the production of HA in various bacterial systems. The use of bacteria for biotechnological production of HA has been advocated for several reasons, technical, economical as well as ethical. The production by Streptococcus spp. has been known for more than 50 years and most of the systems disclosed seem to refer to group A and C streptococci, for instance encapsulated strains of *Streptococcus pyogenes* (group A), which is a human pathogen (Kendall et al (1937)), and *Streptococcus equi* and *Streptococcus equisimilis* (group C), which are animal pathogens. The synthesis of hyaluronic acid as the major capsular polysaccharide in these pathogens is a way to evade host defenses (Roberts et al (1989)).

The biochemistry of HA synthesis in bacteria involves the action of two, sofar known, genes, has A coding for synthase, which is an integral membrane protein and has B coding for UDP-glucose dehydrogenase, which converts UDP glucose to UDP-glucuronic acid. In addition, UDP-glucose needs to be converted to UDP-N-acetyl glucoseamine, which is required for cell wall biosynthesis (see Dougherty and van de Rijn (1992, 1993) and de Angel is et al (1993)). The control of the synthesis, for instance what initiates and terminates HA synthesis, is much less known. However, the stoichiometry of the synthesis provides some guidelines for composition of feed and medium.

The efforts with regard to the development of bacteria-based HA production systems have been focused on the selection of bacteria and suitable culture media. It was early evident that capsulated wildtype strains did not release HA of a molecular weight higher than about 5 million into the fermentation broth, though there were indications in the literature that the actual molecular weight in the capsule might be somewhat higher, see van de Rijn (1983). However, as judged from the literature, including patents and commercially available samples, the molecular weight of bacteria-produced HA is far below that at present produced from rooster combs (see above). It should further be noticed that there often is a very clear difference between high molecular weight values indicated in the literature, which express a desired result, and the values actually obtained.

The highest values obtained in bacteria systems seems to be around 4 million, see for instance U.S. Pat. No. 4,784,990 (Bio-Technology General)—HA of 2–3.5 million.

WO9208799 (Fermentech)—HA of 1–3 million,

JP2058502 (Chisso Corp)—HA of 2–3 million,

JP63129991 and JP63028398 (Denki Kagaku Kogyo KK)—HA of 2–4 millon, and

EP144019 (Miles Laboratories, Mobay Chemical Corp)—HA of 2–4 million.

It should further be noticed that the values given above refer to HA products which have not been sterilized and it's therefore clear that these materials can not be used for the manufacture of HA products which after sterilization have molecular weights comparable to the Healon® products mentioned above.

All strains of streptococci are aerotolerant anaerobes, that is they are able to grow in the presence of oxygen but they don't use oxygen as electron acceptor. Accordingly, the discussion or speculation in prior art articles and patents regarding the importance of air doesn't seem to address any parameter of crucial importance for HA production.

Suitable media and conditions for production of HA are discussed in most of the papers related to HA production, and additional examples of patents or patent applications in this field include JP 63141594 and JP 63123392 (Denki Kagaku Kogyo KK) as well as U.S. Pat. No. 4,897,349 (MedChem Products Inc).

SUMMARY OF THE INVENTION

In spite of the numerous publications indicated above there is still a need for an efficient bacteria based production system for high molecular weight HA products. "High molecular weight" in this connection is meant values exceeding 6 million, in particular over 8 million and especially over 9 million or higher since such a material would be adequate for the manufacture of Healon® GV type products.

I have now found that high molecular weight HA is produced by supercapsulated mutants of streptococcus and one aspect of the invention is the use of such strains in a fermentation system with subsequent purification to obtain HA with molecular weight greater than 6 million, especially greater than 8 or 9 million.

Another aspect of the invention is the preparation and selection of suitable supercapsulated bacteria strains.

DETAILED DESCRIPTION OF INVENTION

The experimental work has been based mainly on the wildtype *S. equi* ss eqrui CCUG 22971, which formed mucoid colonies on agar plates and produced HA in liquid medium. From this species acapsular control mutants as well as supercapsulated mutants were derived. Acapsular mutants banded at a density of 1.09 g/cm$^3$, mucoid wildtypes at 1.05 g/cm$^3$ and supercapsulated strains at a density below 1.03, and more precisely about 1.03–1.02 g/cm$^3$ in Percoll gradients (see the experimental part of the description).

The bacterial strains to be used according to the present invention are streptococci, especially of group A and C, and more particularly *Streptococcus equi*, ss equi mutants, which are supercapsulated species having a capsule about at least twice the size of the capsulated wildtype strains as judged from phase-contrast microscopy and india ink staining of cells growing under optimal conditions. The species banding at a density of or below 1.03 g/cm$^3$, for instance in the range of 1.02–1.03 g/cm$^3$, and produce HA of a molecular weight exceeding 6 million, especially over 8 or most preferably over 9 million.

The method of producing the bacteria strains comprises the steps of subjecting a bacteria strain, such as a wildtype strain of a Lancefield's group C Streptococci, strain *S. erui* ss equi CCUG 22971 to mutagenesis, especially chemical mutagenesis on solid medium avoiding the more cumbersome procedure of mutagenesis in liquid medium, thereby favouring the outgrowth of super mucoid colonies in that the capsule also protects against the mutagenic and toxic chemical and finally enrichment and selection in a density gradient by way of the supercapsulated cells lower density in such a gradient.

*Streptococcus equi* is a horse pathogen currently grouped together with some other pyogenic and hemolytic Streptococci, which belongs to Lancefield's groups C. Other group C streptococci pathogenic for man or animals have been classified as *S.equisimilis*, or as *S.zooepidemicus* mainly from their carbohydrate fermentation pattern. The taxonomic relationships among these strains have not been satisfactorily explored so far and they are only grouped as a taxon Streptococcus sp. (group C) in the First Edition of Bergey's' Manual of Systematic Bacteriology. *S.dysqalactiae*, in contrast, is α-hemolytic and has been recognised as a valid species. It might be most related to *S.equisimilis*. It has also been proposed that S.zooepidimicus is a subspecies of *S.equi*. Accordingly, Streptococcus equi should be referred to as *S.equi ss equi*.

The method of producing HA comprises the steps of (i) selecting a supercapsulated streptococcal strain with the ability to produce HA with molecular weight exceeding 6 million, especially exceeding 8 or 9 million, (ii) cultivating the strain in a bioreactor in the presence of a suitable medium at a temperature below 35° C., preferably in the range of from 30° C. to 35° C., especially 31–33° C. and at a pH-value around or below 6.2, such as 5.6 to 6.2 and preferably in the range of from 5.80 to 5.95, and (iii) purifying the product from the crude mixture.

The medium employed must permit continuous synthesis of hyaluronic acid and not select for non-capsulated cells, which occurs if one tries to optimise the growth rate of cells. It shouldn't contain or release from the reactor any metal ion promoting the degradation of HA, such as iron and copper ions.

The composition of the medium should, in general terms, meet the two requirements of (i) supplying the basic elements (as C, N, O, H, P and S) and necessary growth factors for the build up of the streptococcal cells in correct proportions as well as supplying (ii) the elements and compounds for HA-synthesis in sufficient amounts and correct proportions. The composition of any feed should also meet requirement (ii). The compositions of the growth medium was calculated from the composition of microbial cells and the feed composition from the stoichiometry of the HA-synthesis. The basic liquid medium for fermenter cultivations is given in Table I (see also the experimental section, below).

TABLE I

Compositions of casaminoacids based medium.

| Component | Conc. (g/l) | Standard | Range |
|---|---|---|---|
| Bacto Vitamin Assay Casamino Acids | 12 | | |
| Bacto Yeast Extract | 3 | | ±1 |
| K$_2$HPO$_4$ | 3 | | <+11$^a$ |
| Tryptophan | 0.4 | | |
| MgCl$_2$.6H$_2$O | 0.25 | | |
| MnCl$_2$.6H$_2$O | 0.05 | | |
| NaHCO$_3$ | 2 | | 0–2* |
| Sugar | | Glucose 16 | ±4$^a$ |
| Additions | | as specified | |

*Depending on the desired pH value

The reactor shouldn't be equipped with any type of baffle or internal component causing extensive turbulence and agitation must be provided in a very mild way, for instance by gas lift or by any other type of impeller able to achieve good mixing without generating shear forces. This is of crucial importance in order to obtain very high molecular weights and is contrary to the recommendation given in U.S. Pat. No. 4,784,990, that is "growing with vigorous agitation a microorganism of the genus Streptococcus . . . ".

Various culture alternatives have been tested and found to work, for instance batch, fed batch, semicontinuous fed batch and continuous cultivation.

Media

The standard agar plates used were Blood Agar, BA (prepared from horse blood at the Central Bacteriolgical Laboratory, LU), Bacto Todd Hewitt Agar, THA (Difco) and TYSA made from 10 g/l Bacto Tryptone (Difco), 1 g/l Bacto Yeast Extract (Difco), 1.6 g/l disodium hydrogenphosphate (Merck, PA), 2 g/l sodium hydrogen carbonate (Merck, PA) 0.1 g/l magnesium sulphate (Merck, PA), 20 g/l Bacto Agar (Difco) and 8 g/l sucrose (BDH). Liquid medium for initial tests was Todd Hewitt Broth (Difco) supplemented with Bacto Yeast Extract as above.

Mutagenesis.

Chemical mutagenesis with nitrosoguanidine (Sigma) was employed (Cerda Olmedo IE and Hanwalt PC (1968). The wild type strain was spread on a TYSA plate. A few crystals of nitrosoguanidine was applied in the centre. After incubation a clear zone of inhibition was evident around the nitrosoguanidine crystals. Mucoid colonies growing out in the vicinity of the zone edge were selected and subjected to further testing.

Gradient Centrifugation

The organisms were harvested after growth in THB by centrifugation, washed once in 0.15 M sodium chloride and resuspended in sodium chloride. Percoll gradients were preformed with 10 ml 25–50% Percoll in 0.15 M sodium chloride at 15000 $g_{av}$ for 30 minutes at 4° C. in a fixed angle rotor. Density Marker Beads (Pharmacia LKB Biotechnology AB, Uppsala, Sweden) were added as internal density value standards. A 50 μl volume of the cell suspension was added to each preformed gradient and was then centrifuged at 5000 to 16000 $g_{av}$ for 20 minutes in a swing out rotor at 4° C. (Percoll: Methodology and applications. Pharmacia Laboratory Separation Division).

Estimation of HA Molecular Weights.

One method routinely used comprises comparative electrophoresis using HA references of various molecular weight prepared from rooster combs (Pharmacia Ophthalmics). The references were diluted to contain about 1.1–1.2 mg/ml and were stored in a freezer at −20° C. Gels were cast using 0.7–0.9% agarose. The buffer was phosphate-EDTA (2000 ml, 10× contains: $Na_2HPO_4$ 57.5 g, $NaH_2PO_4$ 13.1 g, $Na_2$ EDTA 3.7 g). References and samples were mixed with bromphenolblue/glycerol and applied to the gel. Samples were allowed to enter the gel from the wells at 20 mA constant current and the gel was then run for about 20 hours at 30 V constant voltage. Finally the gel was stained with a solution of Toluidin blue 0 (0.4%) for 30 min. It was destained in 3% HAc for 15 min and 3–4 times in 1% HAc for 15 min.

Another method employed was SEC-Lalls (Size Exclusion Chromatography-Low Angle Laser Light Scattering). There was good agreement between the two methods up to about 6 million but at higher values the variation was about 10%.

Supercapsulated Strains.

A great number of sequences of the steps specified above have been run in order to select a preferred system for the production of high molecular weight hyaluronic acid and it has been found that the basic step is the selection of the bacteria, which must be supercapsulated. This characteristic can of course be described by using various parameters but we have chosen to use the density value at which the selected strains band as a definition of strains according to the invention. The strains band, as discussed above, at a density equal to or below 1.03 $g/cm^3$, for instance in the range of 1.02–1.03 $g/cm^3$. This definition is of course is valid also in case other methods than density gradient centrifugation is used for the selection of strains.

Supercapsulated strains also have a highly mucoid colony morphology. When plated on TYSA containing 8g sucrose/l very large (>>5 mm diameter) slimy colonies grow out. The thickness of the capsule as measured in the phase contrast microscope is much higher for supercapsulated than for capsulated strains. The diameter of the cells is 1.0±0.2 μm but the capsule diameter is >>4 μm. The two supercapsulated strains further discussed below, H22 and its derivative H22 NO, are both non-hemolytic and have have been found to produce HA of molecular weights up to about 7.5 and 9.5 million, respectively.

Supercapsulation according to the present invention can furthermore be determined by multi variat data analysis of near infrared spectra of whole cells. Analysis of samples according to this method is a well known technique, see for instance Jolliffe IT (1986), Massart et al (1990), Box et al (1978), Mark and Workman (1991), Marshall and Verdun (1990) and Kalias and Lang (1994).

The first principal component (PC1) correlates to the degree of encapsulation and a supercapsulated strain has a first principal component that is ≧0.4, preferably >0.5 and especially >0.7 compared to the first principal component as determined for a weakly capsulated strain examplified by CCUG 23255, CCUG27365 and CCUG27366 (here referred to as reference strains). The absolute value of this principal component depends on the type of strain. In a test mutant H22 (below) had a first principal component of +0.3±0.1 and the corresponding value of H22NO was +0.4±0.05. Under the same experimental conditions the reference strains had PC1 values of −0.2 to −0.3.

Sample preparation comprises growth on blood agar at 37° C., dissolution of a few colonies in 1.5 ml 0.9% NaCl whereafter a 100 microliter cell suspension was spread out to 25×25 mm on an object glass and was allowed to dry in a laminar flow bench. The NIR spectra were collected by reflectance mode (1100–2500 nm) using an InfraAlyzer 500, Bran & Luebbe.

EXAMPLE 1

The supercapsulated mutant *S.equi* ss equi strain H22 was cultivated by fed batch in 1000 ml volume of medium in a Braun Melsungen Fermenter equipped with a modified impeller having a large surface area. The cultivation temperature was 33° C. and pH was maintained at 6.0 by addition of sodium carbonate solution. The feed was started in the beginning of the log. phase (at 4 h) and continued for three hours. The feed rate corresponded to a dilution rate of D=0.02 $h^{-1}$. This feed rate is not optimal for maximal molecular weight, as was found in other experiments. The medium composition was the one given in Table I above. The feed contained sucrose 25 g/l, glucose 10 g/l, mannose 0.1 g/l, $K_2HPO_4$ 3 g/l and yeast extract 4 g/l

TABLE II

Results from fed batch cultivation of strain H22

| Time (h) | $OD_{620}$ | Capsule | Molecular<br>E-fores | Weights ($10^{-6}$)<br>SEC-LALLS | Conc HA<br>(mg/l) |
|---|---|---|---|---|---|
| 0 | 0.146 | −ND | ND | ND | ND |
| 4 | 0.409 | ++ | ND | ND | ND |
| 7 | 0.87 | +++ | 6.8 | 7.1 | 226 |
| 12 | 1.13 | ++ | 6.8 | 7.1 | 376 |
| 14 | 1.15 | ++ | 6.8 | 7.4 | 416 |
| 24 | 1.11 | (+) | 6.3 | 7.5 | 390 |
| 26 | 1.10 | − | 6.5 | 6.4 | 316 |

ND = not determined.

EXAMPLE 2

The strain *S.equi* ss equi H22 was cultivated in an airlift reactor at a temperature of 37° C. using the tryptone based medium (concentrations in g/l).

| | |
|---|---|
| Tryptone | 8 |
| Yeast extract | 3 |
| NaCl | 2 |
| K2HPO4 | 3 |
| MgCl2 | 0.25 |
| MnCl2 | 0.12 |
| NaHCO3 | 2 |
| Glucose | 12 |

When growth had started a "feed" with the composition (conc. in g/l):

Yeast extract (3), Tryptone (8), $K_2HPO_4$ (5) and Sucrose (350) was added.

The "feed" volume was 1100 ml which was added during 10 hours. The operating volume of the reactor was 4500 ml and it was kept constant by a pump connected to a level tube and operating with a high speed. The pH-value was kept at 7.1 by addition of 2M $Na_2CO_3$ during the period of semi-continuous operation. The air was then turned off but the development in the reactor followed for a further 24.5 hours, mainly in order to monitor the degradation of HA. An analysis of the most interesting parameters gave the following results:

| | |
|---|---|
| molecular weight (MDa) | 6.3 (max. value) |
| degradation rate (MDa/h) | 0 (the feed phase) |
| | 0.019 later |
| viscosity at 12 h | 1.504 and |
| HA content (mg/l) | 800 (max value). |

The molecular weight was accordingly above 6 million although neither feed rate nor pH was optimal for high molecular weight formation.

EXAMPLE 3

A continuous cultivation study on the supercapsulated strain H22 NO.

In this experiment a temperature of 33° C., a pH of 6.0 and a constant dilution rate of 0.10 $h^{-1}$ was used. The media used in this experiment at the different steady states varied as follows:

| S.s. No. | Glucose (g/l) | Phosphate (g/l) | PO4/Glu | Yeast extr. (g/l) | YE/Glu | Add. (mg/l) |
|---|---|---|---|---|---|---|
| 1 | 16 | 3.2 | 0.2 | 2.4 | 0.15 | — |
| 2 | 16 | 6.4 | 0.4 | 2.4 | 0.15 | — |
| 3 | 16 | 6.4 | 0.4 | 2.4 | 0.15 | UDP (10) |
| 4 | 16 | 8 | 0.5 | 2.4 | 0.15 | — |
| 5 | 20 | 8 | 0.4 | 2.4 | 0.12 | — |
| 6 | 20 | 8 | 0.4 | 2.4 | 0.12 | RIB (2) | and the results of continuous cultivation were:

| S.s. no. | NU | OD | TS (g/l) | M.w. (MDa) | HA-konc. (mg/l) | $S_{out}$ (g/l) |
|---|---|---|---|---|---|---|
| 1 | 240 | 1.36 | 14.1 | 7.7 | 142 | 0.29 |
| 2 | 228 | 1.30 | 15.1 | 8.7* | 109 | 0.29 |
| 3 | 208 | 1.20 | 15.4 | 9.1 | 124 | 0.26 |
| 4 | 224 | 1.40 | 17.4 | 9.1 | 145 | 0.28 |
| 5 | 288 | 2.45 | 18.6 | 7.1 | 145 | 0.28 |
| 6 | 292 | 3.31 | | 7.0 | 159 | 0.29 |

*an extensively purified sample from this steady state gave a m.w. of 6.1 by Lalls It is evident from the results that the molecular weight in the different steady states was high with 9.1 MDa as the max. value. The yield in this specific example was rather low but in another series of experiments values up to about 350 mg/l have been reached. An increase in the level of phosphate doesn't give a higher yield, but an increase in the molecular weight is observed instead, demonstrating the finding that there is often an inverse relation between yield and molecular weight.

During one week of cultivation the strain was stably non-hemolytic.

It is clear from the experiments indicated above that the new supercapsulated strains are able to produce HA of much higher molecular weight than what has earlier been achieved in bacterial systems. A very promising tool for production of HA has accordingly been developed.

References de Angelis P L, Papaconstatinou J and Weigel (1993), J Biol Chem 268:19181–19184.

Box GEP et al (1978), Statistics for Experimenters, J. Wiley & Sons, ISBN 0-471-09315-7

Brimacombe J S and Webber J M (1964), Mucopolysaccharides, pp 41–49, Elsevier, N.Y.

Cerda-Olmedo I E and Hanwalt P C (1968), J Mol Biol 33:705.

Dougherty B A and van de Rijn (1992), J Exp Med 175:1291–1299.

Dougherty B A and van de Rijn (1993), J Biol Chem 268:7118–7124

Jolliffe I T (1986), Principal component analysis, Springer Verlag, N.Y.

Kalivas J H and Lang P M (1994), Mathmatical analysis of spectral ortogonality, Marcel Dekker Inc, ISBN 0-8247-9155-X Kendall F, Heidelberger M, and Dawson M (1937), J Biol Chem 118:61–69

Mark H and Workman J (1991), Statistics in Spectroscopy, Academic Press

Marshall A G and Verdun F R (1990), Fourier Transforms in NMR, Optical and Mass Spectromety, Elsevier, ISBN 0444-87412-7

Massart et al (1990), Chemometrics: A Textbook (third ed.), Elsevier, ISBN 0-444-42660-4

Roberts I S, Saunders F K and Boulnois G J (1989), Biochem Soc Trans 17:462–464.

What is claimed is:

1. A method for selecting streptococcus strains capable of producing hyaluronic acid with molecular weight exceeding six million, comprising the steps of:

a. subjecting wild type streptococci strains to mutagenesis;

b. thereafter cultivating the strains of streptococci individually in culture medium in a reactor, wherein the culture medium is free of metal ions which promote degradation of hyaluronic acid and does not release from the reactor metal ions which promote the degradation of hyaluronic acid; and c. selecting a supercapsulated mutated strain of a streptococcus from the cultivated strains, the supercapsulated strain having a mucoid morphology and supercapsulated members thereof being capable of forming capsules having a diameter of greater than 4 µm.

2. The method according to claim 1, wherein the supercapsulated members are capable of having a density of no greater than 1.03 g/cm$^3$.

3. The method according to claim 1, wherein the supercapsulated strain is non-hemolytic and produces hyaluronic acid with molecular weight exceeding 6 million.

4. The method according to claim 1, wherein the mutagenesis is chemical mutagensis.

5. The method according to claim 1, wherein the selected supercapsulated streptococcus strain is capable of producing hyaluronic acid having a molecular weight of from 6.3 million to 9.5 million.

6. The method according to claim 5, wherein the selected supercapsulated streptococcus strain is capable of producing hyaluronic acid having a molecular weight exceeding 8 million.

7. The method according to claim 1, wherein the culture medium is free of iron and copper ions.

8. The method according to claim 1, wherein the culture medium has a pH in the range of from 5.6 to 5.95.

9. The method according to claim 8, wherein the culture medium is free of iron and copper ions.

10. The method according to claim 8, wherein the step of cultivating the strains is preformed at a temperature in the range of from 30° C. to 35° C. and in a reactor under agitation conditions substantially free from shear forces.

11. The method according to claim 1, wherein the streptococcus is selected from the group consisting of group A streptococci and group C streptococci.

12. The method according to claim 1, wherein the selected supercapsulated streptococcus strain is non-hemolytic and has a near infrared whole cell spectra first principal component that is greater than or equal to 0.4.

13. A method for selecting streptococcus strains, comprising the steps of:

a. subjecting strains of streptococci to mutagenesis to obtain mutated strains of streptococci;

b. cultivating the mutated strains of streptococci individually in culture medium which is free of iron and copper ions;

b. selecting a supercapsulated strain from among the mutated strains of streptococci, supercapsulated members thereof having a density of no greater than 1.03 g/cm$^3$ and being capable of forming a capsule having a diameter of greater than 4 µm and of producing hyaluronic acid with molecular weight exceeding 6 million.

14. The method according to claim 13, wherein the step of subjecting strains of streptococci to mutagenesis comprises the steps of:

a. plating streptococci on a culture plate;

b. adding crystals of a mutagenic chemical to the culture plate;

c. incubating the culture plate to produce zones of inhibition around the crystals; and d. selecting mutated strains of streptococci growing in the vicinity of the zone edge and having mucoid morphology.

15. The method according to claim 14, wherein the mutagenic chemical is nitrosoguanidine.

16. The method according to claim 13, wherein the selected supercapsulated strain is non-hemolytic and is capable of producing hyaluronic acid with molecular weight of from 6.3 million to 9.5 million.

17. The method according to claim 16, wherein the strains of streptococci subjected to mutagenesis are selected from the group consisting of group A streptococci and group C streptococci.

18. The method according to claim 16, wherein the selected supercapsulated strain is capable of producing hyaluronic acid having a molecular weight exceeding 8 million.

19. The method according to cliam 13, wherein the culture medium has a pH in the range of from 5.6 to 5.95, and further wherein the step of cultivating the strains is perrformed at a temperature in the range of from 30° C. to 35° C. and in a reactor under agitation conditions substantially free from shear forces.

* * * * *

UNITED STATES PATENT AND TRADEMARK OFFICE
CERTIFICATE OF CORRECTION

PATENT NO.    : 6,537,795 B1
DATED         : March 25, 2003
INVENTOR(S)   : Sten Stahl It is certified that error appears in the above-identified patent and that said Letters Patent is hereby corrected as shown below:

<u>Column 10,</u>
Line 6, change "b. selecting" to -- c. selecting --.
Line 37, change "cliam 13" to -- claim 13 --.
Line 39, change "perr-" to -- per- --.

Signed and Sealed this

First Day of July, 2003

JAMES E. ROGAN
*Director of the United States Patent and Trademark Office*